US010350297B2

(12) United States Patent
Craig (10) Patent No.: US 10,350,297 B2
(45) Date of Patent: Jul. 16, 2019

(54) DENTAL MATERIALS AND METHODS (71) Applicant: 3M INNOVATIVE PROPERTIES COMPANY, St. Paul, MN (US)

(72) Inventor: Bradley D. Craig, Lake Elmo, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/521,913

(22) PCT Filed: Oct. 16, 2015

(86) PCT No.: PCT/US2015/055886
§ 371 (c)(1),
(2) Date: Apr. 26, 2017

(87) PCT Pub. No.: WO2016/069290
PCT Pub. Date: May 6, 2016

(65) Prior Publication Data
US 2017/0333297 A1 Nov. 23, 2017

Related U.S. Application Data (60) Provisional application No. 62/073,329, filed on Oct. 31, 2014.

(51) Int. Cl.
| A61K 6/083 | (2006.01) |
| A61K 6/02 | (2006.01) |
| A61K 47/42 | (2017.01) |
| A61K 9/00 | (2006.01) |
| A61K 6/00 | (2006.01) |
| A61K 6/06 | (2006.01) |

(52) U.S. Cl.
CPC ............ *A61K 47/42* (2013.01); *A61K 6/0052* (2013.01); *A61K 6/0073* (2013.01); *A61K 6/0643* (2013.01); *A61K 6/083* (2013.01); *A61K 9/0014* (2013.01)

(58) Field of Classification Search
USPC .................................................. 523/115, 116
See application file for complete search history.

(56) References Cited

U.S. PATENT DOCUMENTS

| 3,066,112 A | 11/1962 | Bowen |
| 3,539,533 A | 11/1970 | Lee, II |
| 3,629,187 A | 12/1971 | Waller |
| 3,709,866 A | 1/1973 | Waller |
| 3,751,399 A | 8/1973 | Lee, Jr. |
| 3,766,132 A | 10/1973 | Lee, Jr. |
| 3,860,556 A | 1/1975 | Taylor |
| 4,002,669 A | 1/1977 | Gross |
| 4,071,424 A | 1/1978 | Dart |
| 4,115,346 A | 9/1978 | Gross |
| 4,259,117 A | 3/1981 | Yamauchi |
| 4,292,029 A | 9/1981 | Craig |
| 4,308,190 A | 12/1981 | Walkowiak |
| 4,327,014 A | 4/1982 | Kawahara |
| 4,379,695 A | 4/1983 | Orlowski |
| 4,387,240 A | 6/1983 | Berg |
| 4,404,150 A | 9/1983 | Tsunekawa |
| 4,503,169 A | 3/1985 | Randklev |
| 4,642,126 A | 2/1987 | Zador |
| 4,652,274 A | 3/1987 | Boettcher |
| 4,695,251 A | 9/1987 | Randklev |
| 5,180,757 A * | 1/1993 | Lucey .................. C08F 290/08 522/76 |
| 5,545,676 A | 8/1996 | Palazzotto |
| 6,030,606 A | 2/2000 | Holmes |
| 6,387,981 B1 | 5/2002 | Zhang |
| 6,572,693 B1 | 6/2003 | Wu |
| 6,624,211 B2 | 9/2003 | Karim |
| 6,730,156 B1 | 5/2004 | Windisch |
| 6,899,948 B2 | 5/2005 | Zhang |
| 7,632,098 B2 | 12/2009 | Falsafi |
| 7,649,029 B2 | 1/2010 | Kolb |
| 7,674,850 B2 | 3/2010 | Karim |
| 7,816,423 B2 | 10/2010 | Karim |
| 7,943,680 B2 | 5/2011 | Bowman |
| 8,236,277 B2 | 8/2012 | Dunbar |
| 8,404,758 B2 | 3/2013 | Bowman |
| 8,455,565 B2 | 6/2013 | Abuelyaman |
| 8,647,510 B2 | 2/2014 | Kolb |

(Continued)

FOREIGN PATENT DOCUMENTS

| EP | 173567 | 3/1986 |
| WO | WO 2001-30305 | 5/2001 |

(Continued)

OTHER PUBLICATIONS

Henn, "Addition of zinc methacrylate in dental polymers: MMP-2 inhibition and ultimate tensile strength evaluation", Clinical Oral Investigations, 2012, vol. 16, pp. 531-536.

Henn, "Characterization of an antimicrobial dental resin adhesive containing zinc methacrylate", Journal of Material Science Materials in Medicine, 2011, vol. 22, pp. 1797-1802.

Yonehara, "A new antifouling paint based on a zinc acrylate copolymer", Progress in Organic Coatings, 2001, vol. 42, pp. 150-158.

International Search Report for PCT International Application No. PCT/US2015/055886, dated Jan. 8, 2016, 5pgs.

*Primary Examiner* — Tae H Yoon (57) ABSTRACT

The present application is directed to a dental material and a method of using the dental material. The dental material can include a hardenable resin; an initiator system; a filler; and from about 1 wt % to about 20 wt % zinc compound, based on the weight of the hardenable resin. The contrast ratio of the cured dental material increases by at least about 10 units after continuous exposure to an aqueous solution for 21 days.

16 Claims, 2 Drawing Sheets

(56) References Cited

U.S. PATENT DOCUMENTS

| | | |
|---|---|---|
| 2005/0020696 A1 | 1/2005 | Montgomery |
| 2008/0206712 A1 | 8/2008 | Craig |
| 2008/0293846 A1 | 11/2008 | Kennard |
| 2009/0208909 A1 | 8/2009 | Rusin |
| 2012/0208965 A1 | 8/2012 | Joly |
| 2013/0006653 A1 | 1/2013 | Mills |
| 2013/0109777 A1 | 5/2013 | Eckert |
| 2013/0157226 A1 | 6/2013 | Zech |

FOREIGN PATENT DOCUMENTS

| | | |
|---|---|---|
| WO | WO 2001-30306 | 5/2001 |
| WO | WO 2001-30307 | 5/2001 |
| WO | WO 2003-063804 | 8/2003 |
| WO | WO 2009-052139 | 4/2009 |
| WO | WO 2010-057144 | 5/2010 |
| WO | WO 2012-003136 | 1/2012 |
| WO | WO 2012-106083 | 8/2012 |
| WO | WO 2012-112304 | 8/2012 |
| WO | WO 2012-112321 | 8/2012 |
| WO | WO 2012-112350 | 8/2012 |
| WO | WO 2013-023138 | 2/2013 |
| WO | WO 2013-028397 | 2/2013 |
| WO | WO 2013-028401 | 2/2013 |
| WO | WO 2013-176870 | 11/2013 |
| WO | WO 2014-074373 | 5/2014 |
| WO | WO 2014-074427 | 5/2014 |
| WO | WO 2014-099317 | 6/2014 |

* cited by examiner

DENTAL MATERIALS AND METHODS

This application is the § 371 U.S. National Stage of International Application No. PCT/US2015/055886, filed 16 Oct. 2015, which claims the benefit of U.S. Provisional Application No. 62/073,392, filed 31 Oct. 2014, the disclosures of which are incorporated by reference herein in their entireties.

BACKGROUND

Dental restorative composites are used extensively in restorative dentistry. In order to cure deeply, the composite materials need to be transparent enough to allow the light to pass through. However, the need for translucency detrimentally impacts the aesthetic characteristics of these composite materials and leads to an unaesthetic restoration. It is therefore desirable to create a better solution to provide deep curing composite formulations with improved aesthetic characteristics.

SUMMARY

Some aspects of the present disclosure provide a dental material. The dental material can include a hardenable resin; an initiator system; a filler; and from about 1 wt % to about 20 wt % zinc compound, based on the weight of the hardenable resin; wherein the contrast ratio of the cured dental material increases by at least about 10 units after continuous exposure to an aqueous solution for 21 days.

Some aspects of the present disclosure provide a method of using a dental material. The method can include providing the dental material of the present disclosure and curing the dental material; wherein the contrast ratio of the cured dental material increases by at least 10 units after continuous exposure to an aqueous solution for 21 days.

Other aspects of the present disclosure provide a method of using a dental material. The method can include providing the dental material, wherein the dental material comprises a hardenable resin, an initiator system, a filler and a zinc compound; and curing the dental material to a depth of at least 4 mm.

Other features and aspects of the present disclosure will become apparent by consideration of the detailed description.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

Hardenable dental restorative composite materials used in larger and deeper increments in the posterior portion of a patient's mouth present a challenge. In order to cure the composite fully at depths of at least 4 mm in these portions, the composite materials need to be transparent enough to allow the initiating photons of light to pass through the material and to sufficiently interact with the initiator system. This need for translucency has limited the aesthetic characteristics of these deep-curing composite materials. Because the contrast ratio (or opacity) of these composite materials is low, the contrast ratio (or opacity) of these composite materials does not fully match the contrast ratio (or opacity) and color of the surrounding natural tooth structure. Therefore, the low contrast ratio (or opacity) detrimentally impacts the aesthetic characteristics of these composite materials.

The present disclosure generally relates to methods of using a dental material, for example, in restorative procedures. Generally, the dental material can include a hardenable resin, an initiator system, a filler and a zinc compound. Generally, the method of using the dental material can include providing the dental material and curing the dental material, wherein the contrast ratio (or opacity) of the cured dental material increases by 10 units after continuous exposure to an aqueous solution for 21 days. As used herein, the aqueous solution includes, but is not limited to water, saliva, artificial saliva or combinations thereof. As used herein, the contrast ratio is calculated as the ratio of the reflectance through a material on a black substrate to the reflectance through an identical material on a white substrate. Particularly, the dental material of current application can, for example, develop additional opacity upon continuous exposure to an aqueous solution for a period of time, while the dental material is highly translucent in the uncured state or cured but prior to exposure to the aqueous solution. This allows for deep or "bulk" curing the dental material and the cured dental material can increase opacity to better match natural dentition over time.

Hardenable Resin

The dental material described herein comprises a hardenable resin. Suitable resins can include thermosetting resins capable of being hardened to form a polymer network. Suitable resins can include ethylenically unsaturated resins, such as acrylate resins, methacrylate resins, epoxy resins, vinyl resins, and mixtures thereof. In some embodiments, the hardenable resin can be made from one or more matrix-forming oligomer, monomer, or polymer, or blends thereof.

In some embodiments, suitable hardenable resins can include hardenable organic resins having sufficient strength, hydrolytic stability, and non-toxicity to render them suitable for use in the oral environment. Examples of such resins include acrylate, methacrylate, urethane, carbamoylsiocyanurate, epoxy resins, and mixtures and derivatives thereof. U.S. Pat. Nos. 3,066,112; 3,539,533; 3,629,187; 3,709,866; 3,751,399; 3,766,132; 3,860,556; 4,002,669; 4,115,346; 4,259,117; 4,292,029; 4,308,190; 4,327,014; 4,379,695; 4,387,240 and 4,404,150 disclose such resins.

One class of hardenable resins is materials having free radically active functional groups and includes monomers, oligomers, and polymers having one or more ethylenically unsaturated groups. In some embodiments, a suitable resin can include at least one ethylenically unsaturated monomer (i.e., includes at least one carbon-carbon double bond). Suitable resin systems may include those described in U.S. Pat. No. 7,816,423. Alternatively, the hardenable resin can be a material from the class of resins that include cationically active functional groups. In another alternative, a mixture of hardenable resins that include both cationically curable and free radically curable resins may be used.

In some such embodiments, the resin system can include a crystalline component to impart the (e.g. a noncovalent) three-dimensional structure for maintaining the initial preformed shape such as described in International Publication No. WO 2010/057144; U.S. Pat. Nos. 7,674,850 and 7,816,423. This crystalline component may or may not have a reactive group capable of polymerizing (also including crosslinking). In some embodiments, the crystalline component can be polymerizable. In some embodiments, the crystalline component can be polymeric (including oligomeric). In some embodiments, the crystalline component can be a polymerizable polymeric material.

In the class of hardenable resins having free radically active functional groups, suitable materials can contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200 to 500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinyl-phthalate. Mixtures of two or more of these free radically hardenable resins can be used if desired.

In some embodiments, suitable hardenable resins can include polymers with low or reduced polymerization stress, such as described in U.S. Pat. Nos. 7,943,680; 8,404,758 and 8,455,565; US Publication No. 2013/0006653; and International Publication Nos. WO2012/003136, WO2012/106083, WO2012/112304, WO2012/112321, WO2012/112350, WO2013/023138, WO2013/028397, WO2013/028401, WO2013/176870, WO 2014/074427, WO 2014/074373 and WO2014/099317. In these embodiments, the dental material of the present disclosure can exhibits relatively low or reduced polymerization stress in addition to improved aesthetic characteristics.

In some embodiments, the dental material is free of TEGDMA.

In some embodiments, the dental material comprises from about 15% to about 45% by weight of hardenable resin, based on total weight of the dental material.

Initiator

The dental material described herein comprises an initiator system. In some embodiments, the initiator system can include one or more initiators and/or a catalyst that enables the composition to be hardened. In some embodiments, the initiator can be a photoinitiator. For example, visible and/or near-infrared photoinitiator systems may be used to initiate photopolymerization in compositions including free-radically polymerizable components. In some such embodiments, the initiator system includes at least one photoinitiator active in the spectral region of about 300 nanometers (nm) to about 1200 nm and capable of promoting free radical polymerization and/or crosslinking of ethylenically unsaturated moieties upon exposure to light of suitable wavelength and intensity. A wide variety of such photoinitiators can be used. Suitable initiators may include those described in U.S. Pat. No. 7,816,423.

In some embodiments, a monomer can be combined with a three component or ternary photoinitiator system including a sensitizer, an electron donor, and an iodonium salt as disclosed, for example, in U.S. Pat. No. 5,545,676. Alternatively, the composition may include a binary initiator system including a sensitizer (e.g., camphorquinone) and an electron donor (e.g., a secondary or a tertiary alkyl amine compound as disclosed, for example, in U.S. Pat. No. 4,071,424).

Another class of useful photoinitiators includes acylphosphine oxides, as disclosed in European Pat. Publ. No. 173,567. Such acylphosphine oxides are of the general formula $(R)_2$-P(O)—CO—R1, wherein each R individually can be a hydrocarbyl group (e.g., alkyl, cycloalkyl, aryl, and aralkyl), which may be substituted with a halo-, alkyl- or alkoxy-group, or the two R groups may be joined to form a ring along with the phosphorous atom, and wherein R1 is a hydrocarbyl group, an S-, O-, or N-containing five- or six-membered heterocyclic group, or a —Z—CO—P(O)—$(R)_2$ group, wherein Z represents a divalent hydrocarbyl group (e.g., alkylene or phenylene) having from 2 to 6 carbon atoms.

Useful acylphosphine oxides can include those in which the R and R1 groups are phenyl or lower alkyl- or lower alkoxy-substituted phenyl. By "lower alkyl" and "lower alkoxy" is meant such groups having from 1 to 4 carbon atoms. The acylphosphine oxide can be bis(2,4,6-trimethylbenzoyl)phenyl phosphine oxide available under the trade designation IRGACURE 819 from Ciba Specialty Chemicals (Tarrytown, N.Y.).

Commercially-available phosphine oxide photoinitiators capable of free-radical initiation when irradiated at wavelengths of greater than 400 to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate.

In some embodiments, the dental material comprises from about 0.05% to about 2.0% by weight of initiator system, based on total weight of the dental material.

Filler

The dental material described herein comprises a filler. Fillers for use in the dental material described herein may be selected from a wide variety of conventional fillers for incorporation into resin systems. In some embodiments, the filler includes one or more conventional materials suitable for incorporation in compositions used for medical applications, for example, fillers currently used in dental restorative compositions. Fillers may be either particulate or fibrous in nature. Suitable filler may include those described in U.S. Pat. No. 7,816,423.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Examples of suitable inorganic fillers are naturally occurring or synthetic materials such as quartz, nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251.

Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Mixtures of these fillers can also be used, as well as combination fillers made from organic and inorganic materials.

Optionally, the surface of the filler particles may be treated with a surface treatment, such as a silane-coupling agent, in order to enhance the bond between the filler and the resin system. The coupling agent may be functionalized with reactive curing groups, such as acrylates, methacrylates, and the like.

The filler particles used to impart a noncovalent structure can be composed of silica, alumina, zirconia, titania, or mixtures of these materials with each other or with carbon. In their synthesized state, these materials are commonly hydrophilic, due to the presence of surface hydroxyl groups. However, the materials may also be modified by treatment with appropriate agents, such as alkyl silanes, in order to modify this character. For example, the surface of a filler particle may be rendered neutral, hydrophobic, or reactive, depending on the desired properties. Fumed silica may be a compound for imparting self-supporting character, due to its low cost, commercial availability, and wide range of available surface character.

Fillers for use in the dental material of the disclosure can be a nanofiller. Suitable nanofillers include either acid reactive or non-acid reactive nanofillers and may include, but are not limited to silica; zirconia; oxides of titanium, aluminum, cerium, tin, yttrium, strontium, barium, lanthanum, zinc, ytterbium, bismuth, iron, and antimony; and combinations thereof. More typical nanofillers may include zirconia ($ZrO_2$); oxides of titanium (e.g., $TiO_2$), and oxides of yttrium (e.g., $Y_2O_3$); and other metal oxides with high refractive indices. As used herein, "high refractive index" means a refractive index of typically at least 1.5, and more typically of at least 2.0. Titania and zirconia are particularly useful nanofillers, as they have very high refractive indices, and will require less weight of material than a lower refractive index material to match the refractive indices appropriately.

The nanofillers typically have an average particle size of at most 100 nanometers and more typically at most 50 nanometers. Such nanofillers typically have an average particle size of at least 2 nanometers, more typically at least 5 nanometers, and even more typically at least 10 nanometers. In some embodiments, the nanofiller is in the form of nanoclusters, typically at least 80 percent by weight nanoclusters. In other embodiments, the nanofiller is in the form of a combination of nanoparticles and nanoclusters. Often a portion of the surface of the nanofiller is silane treated or otherwise chemically treated to provide one or more desired physical properties. Additional suitable nanofillers are disclosed in U.S. Pat. Nos. 6,387,981; 6,572,693; 6,730,156; and 6,899,948; U.S. Publication No. 2008/0293846; as well as International Publication Nos. WO 01/30305, WO 01/30306, WO 01/30307, and WO 03/063804. Filler components described in these references include nanosized silica particles, nanosized metal oxide particles, and combinations thereof.

Typically, the nanofillers of the present disclosure are non-pyrogenic fillers, however pyrogenic fillers can be added as optional additives to the dental compositions.

In some embodiments, the dental material comprises from about 55% to about 85% by weight filler, based on total weight of the dental material.

Zinc Compound

The dental material described herein comprises a zinc compound. As used herein, the term "zinc compound" includes, but is not limited to, zinc salts, zinc complexes, and solvates (e.g., hydrates), thereof. The zinc compound may be polymerizable or non-polymerizable. In some embodiments, the zinc compound is substantially (e.g., fully) or at least partially soluble in the hardenable resin. In some embodiments, the dental material is free of zinc oxide. In some embodiments, the zinc compound is a salt (or a complex) of a carboxylic acid, i.e., an acid which includes a —C(O)OH group. Such a carboxylic acid may include one or more polymerizable groups (e.g., ethylenically unsaturated groups such as acrylate or methacrylate groups), such that the carboxylic acid is an unsaturated carboxylic acid. The unsaturated carboxylic acid used in the current application can be monobasic or polybasic unsaturated carboxylic acid. Suitable monobasic unsaturated carboxylic acid can include, but not limited to acrylic acid and methacrylic acid. Additionally or alternatively, the carboxylic acid may be substituted with one or more polar or hydrophilic groups (including heteroatoms), such that the zinc compound derived from such a carboxylic acid is also relatively polar or hydrophilic. Examples of such polar groups include ether and polyether groups. A non-limiting example of a carboxylic acid substituted with polar groups is 2-(2-methoxy-1-methylethoxy) acetic acid. In some embodiments, the carboxylic acid from which the zinc compound is derived has a pKa of at least about 3.5, at least about 4.0, at least about 4.5, at least about 5.0, or at least about 5.5. In some embodiments, the zinc compound is a zinc salt of acrylic acid or methacrylic acid (i.e., zinc acrylate or zinc dimethacrylate). In some embodiments, the zinc compound has a molecular weight of less than about 500 g/mol, less than about 450 g/mol, less than about 400 g/mol, less than about 350 g/mol, less than about 300 g/mol, less than about 250 g/mol, less than about 200 g/mol. In other embodiments, the zinc compound is a zinc salt of a mineral acid such as for example, nitric or sulfuric acid (i.e., zinc nitrate or zinc sulfate). In still other embodiments, the zinc compound is a salt (or complex) of a phosphoric acid derivative (e.g., a mono- or diester of phosphoric acid such as mono- or di-HEMA phosphate).

In some embodiments, the zinc compound is selected from the group consisting of zinc acrylate, zinc methacrylate, ethylenediaminetetraacetic acid disodium zinc salt, zinc sulfate, and zinc nitrate.

In some embodiments, the dental material comprises from about 1 wt %, 5 wt %, 10 wt %, 20 wt %, or a range between and including any two of these values of zinc compound, based on the weight of the hardenable resin. In some embodiments, the dental material comprises from about 0.15 wt %, 0.75 wt %, 1.5 wt %, 2.25 wt %, 3 wt %, 4.5 wt %, 5 wt %, 9 wt %, 10 wt %, or a range between and including any two of these values of zinc compound, based on total weight of the dental material.

Properties

The dental material comprising the resin, the initiator system, the filler and the zinc compound of the present disclosure can be cured. The cured dental material has an initial contrast ratio (or opacity), which is measured after dental material is cured, but prior to exposure to an aqueous solution. In some embodiments, the initial contrast ratio (or opacity) of cured dental material prior to exposure to the aqueous solution is no more than about 50, about 40, about 30, about 20, or about 10. In some embodiments, the initial contrast ratio (or opacity) of cured dental material prior to exposure to the aqueous solution is about 50, about 40, about 30, about 20, or about 10 or a range between and including any two of these values.

The contrast ratio (or opacity) of the cured dental material of the present disclosure increases upon exposure to an aqueous solution. This allows the cured dental material of the current application to match opacity and color of the surrounding natural tooth structure, thus providing a better aesthetic characteristic. In some embodiments, the contrast ratio (or opacity) of the cured dental material increases by at least about 10 units, about 20 units, about 30 units, about 40 units, or about 50 units after continuous exposure to an aqueous solution at 37° C. for 21 days. In some embodiments, the contrast ratio (or opacity) of cured dental material after continuously exposure to an aqueous solution at 37° C. for 21 days is more than about 50, about 60, about 70, about 80, or about 90.

The contrast ratio (or opacity) of the cured dental material of the present disclosure generally increases initially upon exposure to an aqueous solution, reaches a maximum value, and then generally stabilizes over time. In other words, the contrast ratio (or opacity) increase of the cured dental material upon exposure to the aqueous solution is substantially irreversible.

Method of Use

In some embodiments, the dental material of the present disclosure can be cured. After cured, the dental material can be exposed to an aqueous solution. The contrast ratio (or opacity) of the cured dental material increases by at least 10 units after continuous exposure to an aqueous solution for 21 days.

In some embodiments, a dental material including a hardenable resin, an initiator system, a filler, and a zinc compound can be cured. The dental material is at least partially hardened (e.g., cured) by exposing it to radiation to cause activation of the initiator system. In some other embodiments, the dental material can be completely cured in the mouth by irradiating it with a dental curing light. In these embodiments, the dental material can be cured to a depth of at least 4 mm. After cured, the dental material can be exposed to an aqueous solution. The contrast ratio (or opacity) of the cured dental material increases upon exposure to the aqueous solution. In some embodiments, the contrast ratio (or opacity) of cured dental material after continuously exposure to the aqueous solution for 21 days is more than about 50, about 60, about 70, about 80, or about 90.

The following embodiments are intended to be illustrative of the present disclosure and not limiting.

EMBODIMENTS

Embodiment 1 is a dental material comprising:
  a hardenable resin;
  an initiator system;
  a filler; and
  from about 1 wt % to about 20 wt % zinc compound, based on the weight of the hardenable resin;
  wherein the contrast ratio of the cured dental material increases by at least about 10 units after continuous exposure to an aqueous solution for 21 days.

Embodiment 2 is the dental material of any of embodiment 1, wherein the initial contrast ratio of cured dental material prior to exposure to the aqueous solution is no more than about 50.

Embodiment 3 is the dental material of any of embodiments 1 to 2, wherein the initial contrast ratio of cured dental material prior to exposure to the aqueous solution is no more than about 40.

Embodiment 4 is the dental material of any of embodiments 1 to 3, wherein the initial contrast ratio of cured dental material prior to exposure to the aqueous solution is no more than about 30.

Embodiment 5 is the dental material of any of embodiments 1 to 4, wherein the initial contrast ratio of cured dental material prior to exposure to the aqueous solution is from about 20 to about 40.

Embodiment 6 is the dental material of any of embodiments 1 to 5, wherein the contrast ratio of cured dental material after continuous exposure to the aqueous solution for 21 days is more than about 50.

Embodiment 7 is the dental material of any of embodiments 1 to 6, wherein the contrast ratio of cured dental material after continuous exposure to the aqueous solution for 21 days is more than about 60.

Embodiment 8 is the dental material of any of embodiments 1 to 7, wherein the contrast ratio of cured dental material increases by at least about 20 units after continuous exposure to the aqueous solution for 21 days.

Embodiment 9 is the dental material of any of embodiments 1 to 8, wherein the contrast ratio of cured dental material increases by at least about 30 units after continuous exposure to the aqueous solution for 21 days.

Embodiment 10 is the dental material of any of embodiments 1 to 9, wherein the contrast ratio of cured dental material increases by at least about 40 units after continuous exposure to the aqueous solution for 21 days.

Embodiment 11 is the dental material of any of embodiments 1 to 10, wherein the contrast ratio of cured dental material increases by at least about 50 units after continuous exposure to the aqueous solution for 21 days.

Embodiment 12 is the dental material of any of embodiments 1 to 11, wherein the zinc compound is polymerizable.

Embodiment 13 is the dental material of any of embodiments 1 to 12, wherein the zinc compound is made from a hydrophilic acid or an acid with pKa at least about 3.5.

Embodiment 14 is the dental material of any of embodiments 1 to 13, wherein the zinc compound is a salt of a carboxylic acid.

Embodiment 15 is the dental material of any of embodiments 1 to 14, wherein the carboxylic acid is an unsaturated carboxylic acid.

Embodiment 16 is the dental material of any of embodiments 1 to 15, wherein the unsaturated carboxylic acid is selected from the group consisting of acrylic acid and methacrylic acid.

Embodiment 17 is the dental material of any of embodiments 1 to 16, wherein the zinc compound is a salt of a phosphoric acid.

Embodiment 18 is the dental material of any of embodiments 1 to 17, wherein the zinc compound is selected from zinc nitrate, zinc sulfate, zinc methacrylate, and combinations thereof.

Embodiment 19 is the dental material of any of embodiments 1 to 18, wherein the zinc compound is zinc methacrylate.

Embodiment 20 is the dental material of any of embodiments 1 to 19, wherein the aqueous solution is saliva.

Embodiment 21 is the dental material of any of embodiments 1 to 20, wherein the initiator system is a photoinitiator system.

Embodiment 22 is the dental material of any of embodiments 1 to 21, wherein the dental material is free of TEGDMA.

Embodiment 23 is the dental material of any of embodiments 1 to 22, wherein the contrast ratio increase of the cured dental material upon exposure to the aqueous solution is substantially irreversible.

Embodiment 24 is a method of using a dental material comprising:
providing the dental material of embodiments 1 to 23; and
curing the dental material;
wherein the contrast ratio of the cured dental material increases by at least 10 units after continuous exposure to an aqueous solution for 21 days.

Embodiment 25 is a method of using a dental material comprising:
providing the dental material, wherein the dental material comprises a hardenable resin, an initiator system, a filler and a zinc compound; and
curing the dental material to a depth of at least 4 mm.

Embodiment 26 is the method of any of embodiment 25, wherein the contrast ratio of cured dental material after continuous exposure to an aqueous solution for 21 days is more than about 50.

EXAMPLES

The following examples are given to illustrate, but not limit, the scope of this invention. As used herein, all parts and percentages are by weight unless otherwise specified. All commercial materials were used as obtained from the vendor. Unless otherwise specified, materials can be obtained from Sigma-Aldrich Corp. (St. Louis, Mo.).

Test Methods

Contrast Ratio (CR) Test Method

Resin and paste samples were formed into 1 mm thick by 25.4 mm diameter disks and cured by exposing them to illumination from an LED array (455 nm wavelength, 850 mW/cm$^2$ intensity) for 20 seconds on one side of the disk. ASTM-D2805-95 test method was modified to measure the contrast ratio (or opacity) of the disks. Y-tristimulus values for the disks were measured on an Ultrascan XE Colorimeter (Hunter Associates Laboratory, Reston, Va.) with a 0.953-cm aperture using separate white and black backgrounds. The D65 Illuminant was used with no filters for all measurements. A 10 degree angle of view was used. The contrast ratio, CR, was calculated as the ratio of the reflectance through a material on a black substrate to the reflectance through an identical material on a white substrate. Reflectance is defined as equal to the Y-tristimulus value. Thus, CR=RB/RW, where reflectance through a sample on a black substrate and reflectance through the same sample on a white substrate. Reported CR values are from single measurements with lower values indicative of greater translucency (i.e., transmission of light). In certain instances, CR data was obtained with a Color i7 spectrophotometer (X-Rite, Grand Rapids, Mich.) employing similar methods.

CR values were obtained for each disk after cure. After obtaining an initial CR, the disk was submersed in deionized water at 37° C. Periodically, the disk was removed from the water and dried with a paper towel, the CR re-obtained, and disk re-submersed back in the 37° C. water. In this manner, the changes in CR for the disk as a function of the length of time exposed to water could be monitored.

Depth of Cure (DOC) Test Method

The depth of cure was determined by filling a 4-mm diameter stainless steel mold cavity with the composite (paste), covering the top and bottom of the mold with sheets of polyester film, pressing the sheets to provide a leveled composition surface, placing the filled mold on a white background surface, irradiating the dental composition for 20 seconds using a dental curing light (EPILAR FreeLight2 or EPILAR S-10, available from 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

Diametral Tensile Strength (DTS) Test Method

Diametral tensile strength of a cured composition was measured in this test. An uncured test sample composition was injected into a 4-mm (inside diameter) glass tube and the tube was capped with silicone rubber plugs. The tube was compressed axially at approximately 2.88 kg/cm$^2$ pressure for 5 minutes. The sample was then light cured for 80 seconds by exposure to a XL 1500 dental curing light (3M ESPE, St. Paul, Minn.), followed by irradiation for 90 seconds in a Kulzer UniXS curing box (Heraeus Kulzer GmbH, Germany). The test sample was cut with a diamond saw to form disks about 2.3 mm thick, which were stored in distilled water at 37° C. for about 24 hours prior to testing. Selected samples were stored in distilled water for extended periods (i.e., >24 hours) prior to testing, to study the effect of water exposure on the diametral tensile strength of the cured disks (vide infra).

Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Test results were reported in MPa (megapascals) as the average of multiple measurements.

Materials

"AFM-1" is an addition-fragmentation monomer which can be prepared as described in U.S. Patent Appl. Publication No. 2012/0208965 at paragraph [0078] (Example 1);

"BHT" refers to butylated hydroxytoluene (2,6-di-tert-butyl-4-methylphenol), CAS Reg. No. 128-37-0;

"BisEMA-6" refers to ethoxylated (6 mole ethylene oxide) bisphenol A dimethacrylate as further described in U.S. Pat. No. 6,030,606, available from Sartomer Co., Inc. (Exton, Pa.) as "CD541";

"BisGMA" refers to 2,2-bis[4-(2-hydroxy-3-methacryloyloxypropoxy)phenyl]propane (also referred to as bisphenol A diglycidyl ether methacrylate), CAS Reg. No. 1565-94-2;

"BZT" refers to 2-(2'-hydroxy-5'-methacryloxyethylphenyl)-2H-benzotriazole, CAS Reg. No. 96478-09-0, available from Ciba, Inc. (Tarrytown, N.Y.) as "TINUVIN R 796", also available from Sigma-Aldrich Corp. (St. Louis, Mo.);

"CPQ" refers to camphorquinone, CAS Reg. No. 10373-78-1;

"DPIHFP" or "DPIPF6" refers to diphenyliodonium hexafluorophosphate, CAS Reg. No. 58109-40-3, available from Johnson Matthey, Alfa Aesar Division (Ward Hill, Mass.);

"DDDMA" refers to 1,12-dodecanediol dimethacrylate, CAS Reg. No. 72829-09-5;

"EDMAB" refers to ethyl 4-dimethylaminobenzoate, CAS Reg. No. 10287-53-3;

"ERGP-IEM" refers to 2-propenoic acid, 2-methyl-, 1,1'-[1,3-phenylenebis[oxy-2,1-ethanediyloxy[1-(phenoxymethyl)-2,1-ethanediyl]oxycarbonylimino-2,1-ethanediyl]] ester, CAS Reg. No. 1353886-10-8, which can be prepared as described at paragraph of U.S. Patent Appl. Publication No. 2013/0109777;

"PROCRYLAT" refers to 2,2-bis-4-(3-methacryloxypropoxy)phenyl)propane dimethacrylate, CAS Reg. No. 27689-12-9;

"TEGDMA" refers to triethyleneglycol dimethacrylate, CAS Reg. No. 109-16-0, available from Sartomer Co., Inc. (Exton, Pa.);

"UDMA" refers to diurethane dimethacrylate, CAS Reg. No. 41137-60-4, available under the trade designation "ROHAMERE 6661-0" from Rohm America LLC (Piscataway, N.J.); also available from Dajac Laboratories (Trevose, Pa.);

"$YbF_3$" refers to ytterbium fluoride, 100 nm particle size, available from Sukgyung AT Co. Ltd., (Korea);

"S/T Silica/Zirconia Clusters" refers to silane-treated silica-zirconia nanocluster filler, which can prepared as described in U.S. Pat. No. 6,730,156 at column 25, lines 50-63 (Preparatory Example A) and at column 25, line 64 through column 26, line 40 (Preparatory Example B) with minor modifications. The silanization was performed in water at a pH adjusted to ~8.5 with $NH_4OH$ and the nanocluster filler was obtained by spray drying;

"S/T 20 nm Silica" refers to silane-treated silica nanoparticle filler having a nominal particle size of approximately 20 nanometers, which can be prepared as described in U.S. Pat. No. 6,572,693 at column 21, lines 63-67 (Nano-sized particle filler, Type #2);

"S/T Nanozirconia" refers to silane-treated zirconia nanoparticle filler, which can be prepared from the zirconia sol described in U.S. Pat. No. 8,647,510 at column 31 lines 51-60 (Example 6). The zirconia sol is added to an equivalent weight of 1-methoxy-2-propanol containing 3-methacryloxypropyltrimethoxysilane (1.1 mmol of 3-methacryloxypropyltrimethoxysilane per gram of nanozirconia to be surface treated). The mixture is heated to ~85° C. for 3 hours with stirring. The mixture is cooled to 35° C., adjusted to a pH of ~9.5 with $NH_4OH$, and the mixture reheated to ~85° C. for 4 hours with stirring. The resultant S/T Nanozirconia is isolated by removing solvents via gap drying. S/T Nanozirconia may also be prepared as described in U.S. Pat. No. 7,649,029 beginning at column 19, line 39 through column 20, line 41 (Filler I), except for the substitution of 3-methacryloxypropyltrimethoxysilane for the blend of Silquest A-174 and A-1230, and further removing the solvents via gap drying.

"S/T Filler" refers to zirconia-silica filler (which can be prepared as described in U.S. Pat. No. 6,624,211 at column 15, line 60 through column 16, line 28) silane-treated in the following manner. One hundred parts of the filler (average particle size 0.6-0.9 micrometers) was mixed with deionized water at a solution temperature of between 20-30° C., and the pH was adjusted to 3-3.3 with trifluoroacetic acid (0.278 parts). 3-Methacryloxypropyltrimethoxysilane (available from Wacker Chemie A G, Munich, Germany) was added to the slurry in an amount of 7 parts, and the blend was mixed for 2 hours. At the end of 2 hours, the pH was neutralized with calcium hydroxide. The filler was dried, crushed and screened through a 74 micron screen.

Other Materials

As more fully detailed below, resin and paste materials which included various commercially available and experimentally prepared metal-containing additives were prepared and evaluated. The following metal-containing additives were purchased from commercial suppliers such as Sigma-Aldrich (St. Louis, Mo.), Johnson Matthey, Alfa Aesar Division (Ward Hill, Mass.), TCI America (Portland, Oreg.), or Chem Service (West Chester, Pa.) and were used as received: zinc methacrylate ("ZnMA", CAS Reg. No. 13189-00-9), calcium methacrylate ("CaMA", CAS Reg. No. 16809-88-4), sodium methacrylate ("NaMA", CAS Reg. No. 5536-61-8), aluminum methacrylate ("AlMA", CAS Reg. No. 21828-44-4), yttrium methacrylate ("YMA", CAS Reg. No. 79718-33-5), zirconium methacrylate ("ZrMA"), magnesium methacrylate ("MgMA", CAS Reg. No. 7095-16-1), zinc nitrate hexahydrate ($Zn(NO_3)_2.6H_2O$, CAS Reg. No. 10196-18-6, zinc sulfate, zinc oleate (CAS Reg. No. 557-07-3), ethylenediaminetetraacetic acid disodium zinc salt tetrahydrate ($Na_2Zn(EDTA).4H_2O$, CAS Reg. No. 176736-49-5), and zinc acetylacetonate hydrate (Zn (acac)$_2$).x$H_2O$, CAS Reg. No. 108503-47-5. Other zinc-containing additives were prepared as follows, and used directly as reaction products without further purification.

Reaction Product 1 (ZnO+MMEAA)

Zinc oxide (1.9941 g) was digested into 2-(2-methoxy-1-methylethoxy)acetic acid (7.326 g, "MMEAA", prepared as described in U.S. Pat. No. 8,236,277 beginning at column 11, line 1, through column 12, line 2). The mixture was heated at 100° C. under vacuum until water evolution ceased (~1-2 hours).

Reaction Product 2 (ZnO+HEMA Phosphate)

Zinc oxide (4.99 g) was digested into HEMA-phosphate (26.0 g, which may be prepared as a mixture of mono-, di-, tri-HEMA phosphate and tetra-HEMA pyrophosphate in the manner described at columns 24-25 of U.S. Pat. No. 7,632,098 for "HEMA-P"; bis(methacryloxyethyl)phosphate available from Nippon Kayaku (Japan) under the trade designation KAYAMER PM-2 may also be used). The mixture was heated at 100° C. under vacuum until water evolution ceased (~1-2 hours).

Preparation of Photocurable Stock Resins, Resins A-C

Photocurable stock resins (Resins A-C) were prepared by hand mixing the components shown in Table 1 to form a uniform mixture.

TABLE 1

Photocurable Stock Resin Formulations, Resins A-C

| Component | Resin A, wt. % | Resin B, wt. % | Resin C, wt. % |
|---|---|---|---|
| UDMA | 34.48 | 18.76 | — |
| PROCRYLAT | 42.36 | — | — |
| BisEMA-6 | 10.84 | — | — |
| BisGMA | 10.84 | — | 49.24 |
| ERGP-IEM | — | 68.85 | — |
| DDDMA | — | 8.65 | — |
| AFM-1 | — | 1.51 | — |
| TEGDMA | — | — | 49.24 |
| BHT | 0.090 | 0.050 | — |
| BZT | 0.600 | 0.500 | — |
| CPQ | 0.130 | 0.281 | 0.22 |
| EDMAB | 0.380 | 1.100 | 1.00 |
| DPIHFP | 0.280 | 0.298 | 0.30 |

Preparation of Photocurable Experimental Resins

Experimental resins were prepared by hand mixing one of the stock resins in Table 1 (i.e., Resin A, B, or C) with one of the metal-containing additives to a uniform mixture, in the amounts shown in Table 2.

TABLE 2

Photocurable Experimental Resin Formulations

| | Resin Components | |
|---|---|---|
| Resin ID | Metal-containing additive (wt. %) | Stock Resin (wt. %) |
| Resin 1 | ZnMA (20) | Resin C (80) |
| Resin 2 | ZnMA (2.5) | Resin A (97.5) |
| Resin 3 | ZnMA (5) | Resin A (95) |
| Resin 4 | ZnMA (7.5) | Resin A (92.5) |
| Resin 5 | ZnMA (10) | Resin A (90) |
| Resin 6 | ZnMA (15) | Resin A (85) |
| Resin 7 | ZnMA (20) | Resin A (80) |
| Resin 8 | ZnMA (5) | Resin B (95) |
| Resin 9A | CaMA (10) | Resin A (90) |
| Resin 9B | NaMA (10) | Resin A (90) |
| Resin 9C | ZrMA (10) | Resin A (90) |
| Resin 9D | YMA (10) | Resin A (90) |
| Resin 9E | MgMA (10) | Resin A (90) |
| Resin 9F | AlMA (10) | Resin A (90) |
| Resin 10 | $Zn(NO_3)_2 \cdot 6H_2O$ (10) | Resin A (90) |
| Resin 11 | $Na_2Zn(EDTA) \cdot 4H_2O$ (10) | Resin A (90) |
| Resin 12 | $ZnSO_4$ (10) | Resin A (90) |
| Resin 13 | $Zn(MEEAc)_2$ (10) | Resin A (90) |
| Resin 14 | $Zn(MEEAc)_2$ (20) | Resin A (80) |
| Resin 15 | Reaction Product 1 (10) | Resin A (90) |
| Resin 16 | Reaction Product 1 (20) | Resin A (80) |
| Resin 17 | Reaction Product 2 (10) | Resin A (90) |
| Resin 18 | Reaction Product 2 (20) | Resin A (80) |

Preliminary Studies

Resin 1, which included 20 wt. % ZnMA, was placed into a small metal mold between two polyester sheets and the resin irradiated with a dental curing light (EPILAR S-10, available from 3M ESPE Dental Products) for 20 seconds. Two disks (each ~8 mm diameter×~1 mm thick) were prepared in this manner. Both of the disks were translucent and colorless after curing. One of the disks was left dry in air under ambient conditions as a control, while the other disk was submersed into deionized water at 37° C. After 4 days, water-exposed disk was removed and evaluated. The water-exposed disk was white and opaque in appearance. In contrast, the control disk remained substantially unchanged from its original appearance immediately after cure.

The opacity change due water exposure was determined to be substantially irreversible: heating the water-exposed disk at 100° C. for 2 hours resulted in no reduction in opacity.

CR Studies of Resins and Pastes with Metal-Containing Additives

The affect of water exposure on cured disks of the resins in Table 2 was evaluated by measuring the CR of the disks, before and after exposure to water (via submersion) at 37° C. Multiple CR measurements were obtained over time (i.e., at various lengths of water exposure). CR Measurement results are presented in FIG. 1 and Table 3.

TABLE 3

Contrast Ratio (CR) Measurement Data for Photocured Experimental Resins

| Resin ID | Starting Contrast Ratio (prior to water exposure) | Contrast Ratio after 10 days exposure to water at 37° C. | Contrast Ratio after 21 days exposure to water at 37° C. | Contrast Ratio Change (after 21 days) |
|---|---|---|---|---|
| Resin A (Control) | 15.96 | 15.88 | 15.68* | −0.28 |
| Resin 3 | 25.79 | 82.99* | 73.62 | 47.83 |
| Resin 5 | 42.60 | 76.06* | 93.33 | 50.73 |
| Resin 6 | 48.23 | 81.01* | 93.82 | 45.59 |
| Resin 7 | 54.41 | 85.78* | 97.09 | 42.68 |
| Resin 8 | 32.08 | 69.96 | 67.84 | 35.76 |
| Resin 9A | 69.68 | 52.97 | 51.84 | −17.84 |
| Resin 9B | 63.88 | 69.88 | 72.89 | 9.01 |
| Resin 9C | 16.73 | 17.09* | 16.88 | 0.15 |
| Resin 9D | 26.54 | 38.37* | 33.10 | 6.56 |
| Resin 9E | 49.90 | 58.95 | 58.26* | 8.36 |
| Resin 9F | 33.21 | 34.46 | 35.66* | 2.45 |
| Resin 10 | 19.67 | 34.12* | 37.47 | 17.80 |
| Resin 11 | 17.43 | 30.46* | 31.93 | 14.50 |
| Resin 12 | 50.13 | 66.15* | 67.22 | 17.09 |
| Resin 13 | 10.03 | 16.95 | 18.10 | 8.07 |
| Resin 14 | 13.59 | 75.74 | 74.26 | 60.67 |
| Resin 15 | 29.83 | 46.08 | 48.83 | 19.00 |
| Resin 16 | 51.76 | 64.49 | 67.07 | 15.31 |
| Resin 17 | 9.52 | 17.74 | 20.49 | 10.97 |
| Resin 18 | 9.95 | 18.99 | 24.66 | 14.71 |

*Calculated based on polynomial fit of multiple CR measurements over time.

Figure 1:
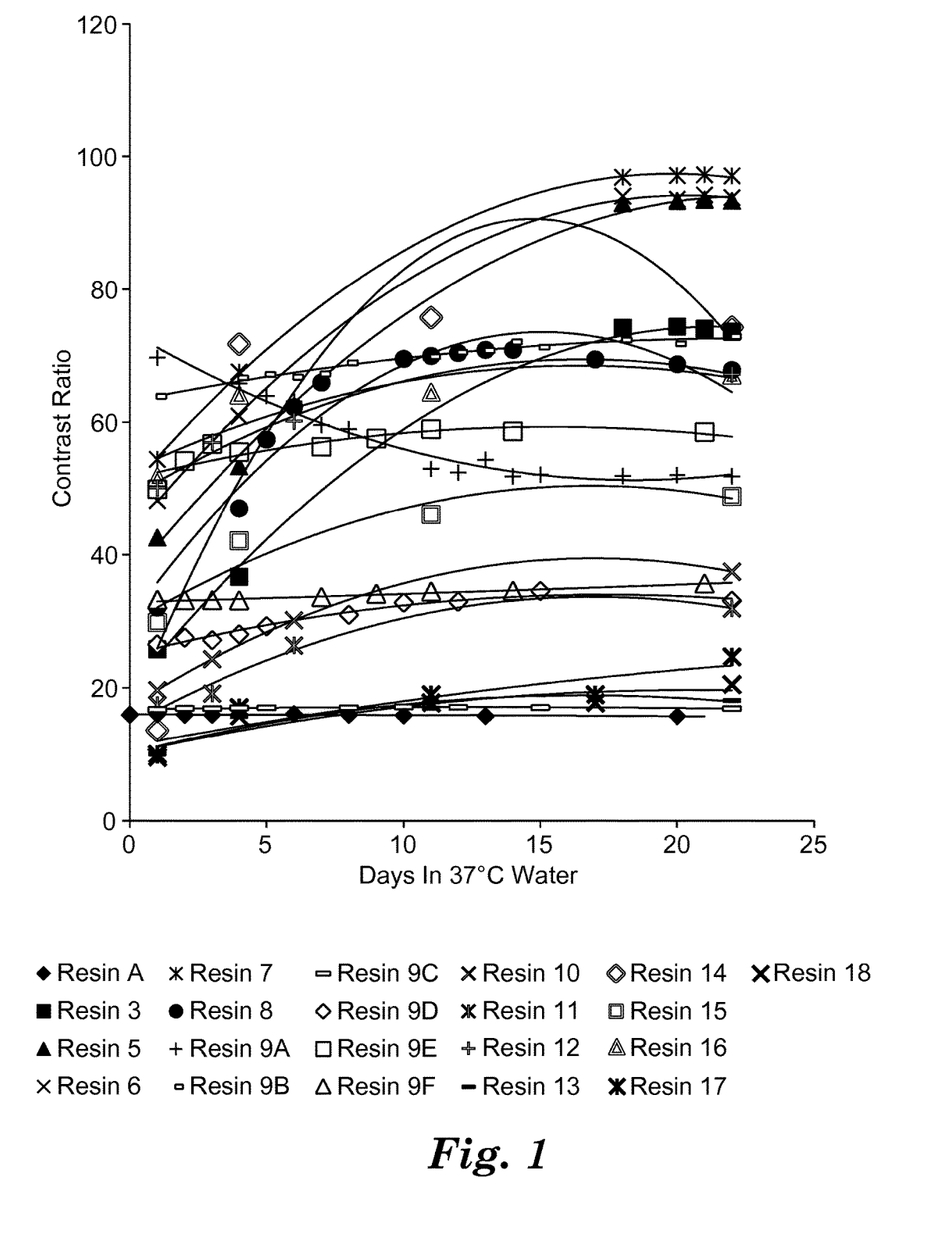
FIG. 1 is a polynomial fit of multiple contrast ratio measurements for photocured experimental resins over time.

From the data in FIG. 1 and Table 3, a number of observations can be made. First, the control (i.e., cured Resin A), which lacked any metal-containing additive, displayed essentially no change in CR after extended exposure to water. In contrast, the CRs of the cured resin disks which included ZnMA in their resin formulations displayed a significant increase after exposure to water (e.g., cured disks of Resin 3, Resin 5, Resin 6, Resin 7, and Resin 8). The CRs of the cured ZnMA-containing resin disks generally increased initially and then stabilized over time. For example and referring to FIG. 1, the cured disk of Resin 5 displayed an initial CR of 42.60 (prior to water exposure), a CR of 67.54 after 3 days of water exposure, a CR of 96.88 after 17 days of water exposure, a CR of 97.14 after 19 days of water exposure, and a CR of 97.09 after 21 days of water exposure. Even after exposure to 37° C. water for 158 days, the CR of the cured resin disk from Resin 5 was 89.08 (data not shown). In contrast, cured resins which included methacrylates of other metals (e.g., Resins 9A-9F) did not display significant increases in opacity with water exposure. In the case of the cured disk of Resin 9A, a decrease of opacity was observed after 10 or 21 days of water exposure, in comparison to cured disk prior to water exposure. Comparison of cured disks from Resin 3 and Resin 8 show that different resin systems may be used in conjunction with ZnMA (i.e., Resin A and Resin B, respectively). It is also apparent from the results in FIG. 1 and Table 3, that the zinc-containing additive in the resin can, but need not, contain polymerizable groups such as methacrylate groups to display aqueous opacification effects. For example, zinc salts of mineral acids such as zinc nitrate and zinc sulfate, may be included in resin systems (i.e., Resin 10 and Resin 12). Zinc additives with hydrophilic ligands/anions (or ligands/anions substituted with polar groups and/or heteroatoms) may be used with good effect (e.g., $Na_2Zn(EDTA)$-containing Resin 11, as well as Resins 15-18), while the effect zinc compounds with relatively non-polar groups (zinc oleate-containing Resin 12) are less effective. Comparison of the cured resin disks derived from Resin 13 and Resin 14 show that, increasing the loading of a given zinc compound (e.g., $Zn(MEEAc)_2$) in a particular resin system can provide a substantially increased ability of the corresponding cured resin to opacify with water exposure.

Preparation of Photocurable Composite Pastes, Pastes 1-9

Composite pastes (Pastes 1-9) with variable ZnMA loading, resin packages, and filler packages were prepared by handing mixing the components shown in Table 5 to form a uniform mixture.

TABLE 5

Photocurable Paste Formulations for Pastes 1-9

| Paste ID | Resin, wt. % (Resin ID) | YbF$_3$, wt. % | S/T Filler, wt. % | Fillers S/T Silica/ Zirconia Clusters, wt. % | S/T 20 nm Silica, wt. % | S/T Nano- zirconia, wt. % |
|---|---|---|---|---|---|---|
| Paste 1 | 35.52 (Resin 2) | 7.00 | 57.48 | — | — | — |
| Paste 2 | 35.51 (Resin 3) | 6.99 | 57.49 | — | — | — |
| Paste 3 | 35.30 (Resin 4) | 7.49 | 57.21 | — | — | — |
| Paste 4 | 35.47 (Resin 5) | 7.03 | 57.49 | — | — | — |
| Paste 5 | 35.50 (Resin 6) | 7.00 | 57.50 | — | — | — |
| Paste 6 | 35.53 (Resin 7) | 7.00 | 57.47 | — | — | — |
| Paste 7 | 25.20 (Resin 8) | 5.60 | — | 64.68 | 2.95 | 1.57 |
| Paste 8 | 25.06 (Resin 8')* | 5.62 | — | 64.81 | 2.93 | 1.58 |
| Paste 9 | 25.03 (Resin 8")** | 5.63 | — | 64.84 | 2.93 | 1.57 |

*Resin 8': Resin B (90.8 wt. %) + ZnMA (9.2 wt. %)
*Resin 8": Resin B (84.5 wt. %) + ZnMA (15.5 wt. %)

As for the resins previously described, CR measurements were made on disks of the light cured pastes, before and after exposure to water at 37° C. Results are presented in FIG. 2 and Table 6.

TABLE 6

Contrast Ratio Measurement Data for Photocured Experimental Paste Formulations, Pastes 1-9

| Example | Paste ID | ZnMA in Resin/Paste, wt. % | Starting Contrast Ratio | Contrast Ratio after 21 days exposure to water at 37° C. | Contrast Ratio Change (after 21 days) |
|---|---|---|---|---|---|
| CE1 | Paste 1 | 2.5/0.89 | 41.60 | 40.03 | −1.60 |
| EX1 | Paste 2 | 5/1.78 | 42.00 | 52.84 | 10.84 |
| EX2 | Paste 3 | 7.5/2.65 | 43.63 | 64.79 | 21.16 |
| EX3 | Paste 4 | 10/3.55 | 45.40 | 71.84 | 26.44 |

TABLE 6-continued

Contrast Ratio Measurement Data for Photocured Experimental Paste Formulations, Pastes 1-9

| Example | Paste ID | ZnMA in Resin/Paste, wt. % | Starting Contrast Ratio | Contrast Ratio after 21 days exposure to water at 37° C. | Contrast Ratio Change (after 21 days) |
|---|---|---|---|---|---|
| EX4 | Paste 5 | 5.33/15 | 55.30 | 84.19 | 28.89 |
| EX5 | Paste 6 | 7.11/20 | 56.00 | 87.60 | 31.60 |
| CE2 | Paste 7 | 5/1.26 | 37.50 | 37.45 | −0.05 |
| CE3 | Paste 8 | 9.2/2.30 | 38.01 | 40.22* | 2.21 |
| EX6 | Paste 9 | 15.5/3.88 | 39.65 | 56.03* | 16.38 |

*Calculated based on polynomial fit of multiple data points.

Figure 2:
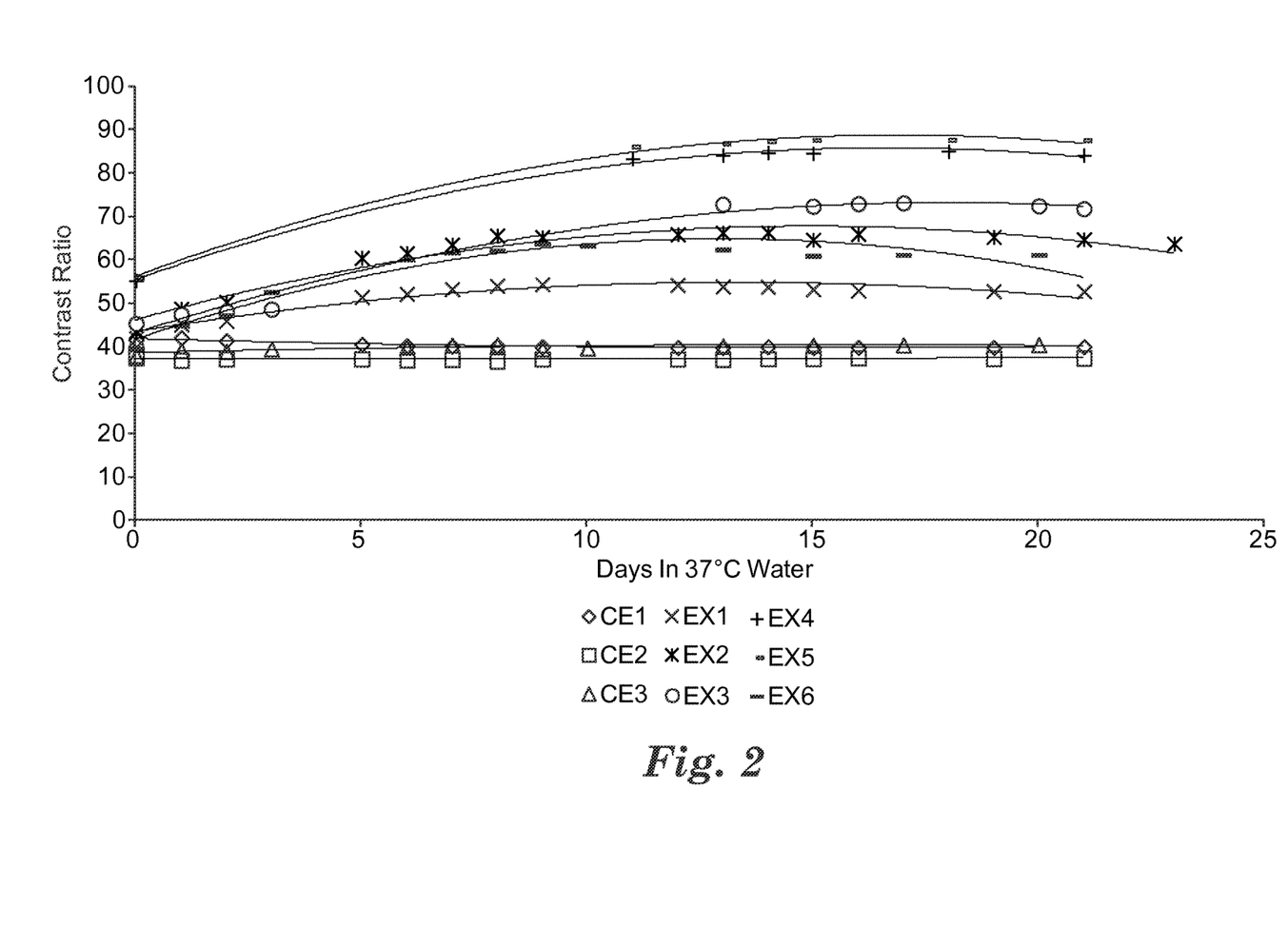
FIG. 2 is a polynomial fit of multiple contrast ratio measurements for photocured experimental composite pastes over time

It is evident from the data in FIG. 2 and Table 6, that for ZnMA containing pastes, significant changes in CR are not observed for cured composite materials which include relatively low weight percents of ZnMA in the uncured paste (e.g., CE1, CE2, CE3). In contrast, paste materials with relatively higher loadings of ZnMA do display substantial opacification, after curing and water exposure (e.g., EX1-EX6).

As shown in Table 7 below, the pastes could be readily be light cured at a depth greater than 4 mm.

TABLE 7

Depth of cure data for Pastes

| Paste ID | Depth of Cure, mm |
|---|---|
| Paste 1 | 4.715 |
| Paste 2 | 4.65 |
| Paste 3 | 4.64 |
| Paste 4 | 4.495 |
| Paste 7 | 5.165 |
| Paste 8 | 5.00 |
| Paste 9 | 5.17 |

The diametral tensile strengths of cured experimental pastes were evaluated. As shown in Table 8, the tensile strengths of the cured experimental pastes were comparable to that of a control, and thus displayed sufficient strength to be used in an oral environment. Notably, the tensile strength of the cured pastes did not degrade after extended exposure to water/opacificatication (e.g., Paste 9).

TABLE 8

Diametral Tensile Strength Data for Pastes

| Paste ID | DTS, MPa (Std Dev) |
|---|---|
| Filtek Bulk Fill, U shade (control, available from 3M ESPE, St. Paul, MN) | 75.55 (4.12) |
| Paste 1 | 77.42 (10.11) |
| Paste 2 | 72.35 (4.55) |
| Paste 3 | 70.73 (3.89) |
| Paste 7 | 77.99 (3.39) |
| Paste 8 | 75.20 (3.29) |
| Paste 9 | 70.87 (3.14)* |

*71.67 (2.70) after submersion for 7 days in water at 37° C.

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A dental material comprising:
   a hardenable resin;
   an initiator system, the initiator system comprising camphorquinone;
   a filler, the filler comprising silica particles, metal oxide particles, and combinations thereof; and
   from about 1 wt % to about 20 wt % zinc compound, based on the weight of the hardenable resin, the zinc compound comprising an acrylate group, a methacrylate group, or combinations thereof;
   wherein the contrast ratio of the dental material when cured increases by at least 10 units after continuous exposure to an aqueous solution for 21 days, and
   wherein the dental material is free of TEGDMA.

2. The dental material of claim 1, wherein the initial contrast ratio of the dental material when cured prior to exposure to the aqueous solution is no more than 50.

3. The dental material of claim 1, wherein the initial contrast ratio of the dental material when cured prior to exposure to the aqueous solution is no more than 40.

4. The dental material of claim 1, wherein the initial contrast ratio of the dental material when cured prior to exposure to the aqueous solution is no more than 30.

5. The dental material of claim 1, wherein the initial contrast ratio of the dental material when cured prior to exposure to the aqueous solution is from 20 to 40.

6. The dental material of claim 1, wherein the contrast ratio of the dental material when cured after continuous exposure to the aqueous solution for 21 days is more than 50.

7. The dental material of claim 1, wherein the contrast ratio of the dental material when cured after continuous exposure to the aqueous solution for 21 days is more than 60.

8. The dental material of claim 1, wherein the contrast ratio of the dental material when cured increases by at least 20 units after continuous exposure to the aqueous solution for 21 days.

9. The dental material of claim 1, wherein the contrast ratio of the dental material when cured increases by at least 30 units after continuous exposure to the aqueous solution for 21 days.

10. The dental material of claim 1, wherein the contrast ratio of the dental material when cured increases by at least 40 units after continuous exposure to the aqueous solution for 21 days.

11. The dental material of claim 1, wherein the contrast ratio of the dental material when cured increases by at least 50 units after continuous exposure to the aqueous solution for 21 days.

12. The dental material of claim 1, wherein the zinc compound is selected from zinc acrylate and zinc methacrylate.

13. The dental material of claim 1, wherein the zinc compound is zinc methacrylate.

14. The dental material of claim 1, wherein the aqueous solution is saliva.

15. The dental material of claim 1, wherein the contrast ratio increase of the dental material when cured upon exposure to the aqueous solution is substantially irreversible.

16. A method of using a dental material comprising:
    providing the dental material of claim 1; and
    curing the dental material;
    wherein the contrast ratio of the dental material when cured increases by at least 10 units after continuous exposure to an aqueous solution for 21 days.

* * * * *

UNITED STATES PATENT AND TRADEMARK OFFICE
CERTIFICATE OF CORRECTION

PATENT NO. : 10,350,297 B2
APPLICATION NO. : 15/521913
DATED : July 16, 2019
INVENTOR(S) : Bradley Craig Page 1 of 1

It is certified that error appears in the above-identified patent and that said Letters Patent is hereby corrected as shown below:

On the Title Page

Column 1, (Assignee)
Line 1, delete "iNNOVATIVE" and insert -- INNOVATIVE --, therefor.

In the Specification

Column 1
Line 52, delete "time" and insert -- time. --, therefor.

Column 2
Lines 58-59, delete "carbamoylsiocyanurate," and insert -- carbamoylisocyanurate, --, therefor.

Column 12
Line 15, delete "A G," and insert -- AG, --, therefor.

Signed and Sealed this
Sixteenth Day of June, 2020

Andrei Iancu
*Director of the United States Patent and Trademark Office*